United States Patent
Matsunaga et al.

(10) Patent No.: US 9,192,356 B2
(45) Date of Patent: Nov. 24, 2015

(54) ULTRASOUND DIAGNOSIS APPARATUS

(75) Inventors: Satoshi Matsunaga, Nasushiobara (JP); Masatoshi Nishino, Otawara (JP); Jiro Higuchi, Otawara (JP); Osamu Nakajima, Otawara (JP); Yoshihiro Oomori, Otawara (JP); Tomokazu Fujii, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/356,123

(22) Filed: Jan. 23, 2012

(65) Prior Publication Data
US 2012/0203106 A1    Aug. 9, 2012

(30) Foreign Application Priority Data

Feb. 3, 2011 (JP) ................. 2011-021601

(51) Int. Cl.
*A61B 8/00* (2006.01)
*A61B 8/06* (2006.01)
*A61B 8/08* (2006.01)

(52) U.S. Cl.
CPC . *A61B 8/465* (2013.01); *A61B 8/06* (2013.01); *A61B 8/463* (2013.01); *A61B 8/469* (2013.01); *A61B 8/488* (2013.01); *A61B 8/54* (2013.01); *A61B 8/56* (2013.01)

(58) Field of Classification Search
CPC .......... A61B 8/465; A61B 8/06; A61B 8/469; A61B 8/488; A61B 8/54; A61B 8/56; A61B 8/463
USPC ................................. 600/437–469
See application file for complete search history.

(56) References Cited

U.S. PATENT DOCUMENTS 5,293,326 A * 3/1994 Arima et al. ............... 702/39
5,481,917 A * 1/1996 Arima et al. .............. 73/621
(Continued)

FOREIGN PATENT DOCUMENTS

CN    1636520 A    7/2005
CN    1768709 A    5/2006
(Continued)

OTHER PUBLICATIONS

Office Action mailed Dec. 2, 2013 in Chinese Application No. 201210023405.8.
(Continued)

*Primary Examiner* — Sanjay Cattungal
(74) *Attorney, Agent, or Firm* — Oblon, McClelland, Maier & Neustadt, L.L.P.

(57) ABSTRACT

The ultrasound diagnosis apparatus according to the embodiment includes an ultrasound probe that transmits and receives ultrasound waves to and from a subject, and generates and displays images of the inside of the subject based on the reception results from the ultrasound probe. The ultrasound diagnosis apparatus includes a memory, a detector, a selection part, and a processor. The memory stores association information that associates positions in real space with examination conditions including image quality conditions and/or application type. The detector detects the position of the ultrasound probe in real space. The selection part selects examination conditions corresponding to the detected position based on the association information. The processor performs processing based on the selected examination conditions.

16 Claims, 10 Drawing Sheets

(56) References Cited

U.S. PATENT DOCUMENTS

| | | | |
|---|---|---|---|
| 7,074,185 B2 * | 7/2006 | Takeuchi | 600/437 |
| 7,513,872 B2 * | 4/2009 | Baba et al. | 600/455 |
| 7,871,379 B2 * | 1/2011 | Ohtsuka | 600/443 |
| 8,007,439 B2 * | 8/2011 | Specht | 600/459 |
| 8,125,311 B2 * | 2/2012 | Takimoto et al. | 340/5.2 |
| 8,303,507 B2 * | 11/2012 | Baba et al. | 600/453 |
| 2004/0019270 A1 * | 1/2004 | Takeuchi | 600/407 |
| 2005/0085728 A1 * | 4/2005 | Fukuda | 600/449 |
| 2005/0090742 A1 * | 4/2005 | Mine et al. | 600/443 |
| 2006/0052704 A1 * | 3/2006 | Baba et al. | 600/453 |
| 2006/0072124 A1 * | 4/2006 | Smetak et al. | 356/614 |
| 2006/0084873 A1 * | 4/2006 | Baba et al. | 600/441 |
| 2006/0100521 A1 * | 5/2006 | Takeuchi | 600/462 |
| 2007/0010743 A1 * | 1/2007 | Arai | 600/443 |
| 2007/0038086 A1 * | 2/2007 | Ohtsuka | 600/437 |
| 2007/0239004 A1 | 10/2007 | Kakee et al. | |
| 2008/0097205 A1 * | 4/2008 | Takimoto et al. | 600/437 |
| 2009/0137907 A1 * | 5/2009 | Takimoto et al. | 600/461 |
| 2009/0209859 A1 * | 8/2009 | Tsujita et al. | 600/445 |
| 2009/0275833 A1 | 11/2009 | Ikeda et al. | |
| 2009/0299185 A1 * | 12/2009 | Oikawa et al. | 600/447 |
| 2010/0022871 A1 * | 1/2010 | De Beni et al. | 600/424 |
| 2011/0026796 A1 * | 2/2011 | Hyun et al. | 382/131 |
| 2013/0142010 A1 * | 6/2013 | Ajiki | 367/7 |
| 2013/0144168 A1 * | 6/2013 | Yoneyama | 600/443 |

FOREIGN PATENT DOCUMENTS

| | | |
|---|---|---|
| CN | 1973776 A | 6/2007 |
| CN | 101002681 A | 7/2007 |
| CN | 101695451 A | 4/2010 |
| JP | 8-191832 | 7/1996 |
| JP | 10-328180 | 12/1998 |
| JP | 2001-137237 | 5/2001 |
| JP | 2005-118142 | 5/2005 |
| JP | 2005-529701 | 10/2005 |
| JP | 2008-212508 | 9/2008 |
| JP | 2010-69018 | 4/2010 |
| JP | 2010-119576 A | 6/2010 |
| JP | 2010-259662 A | 11/2010 |
| WO | WO 03/107251 | 12/2003 |

OTHER PUBLICATIONS

Office Action issued on Aug. 26, 2014 in the corresponding Japanese Patent Application No. 2011-021601.

Office Action issued Apr. 9, 2015 to Chinese Patent Application No. 201210023405.

* cited by examiner

ULTRASOUND DIAGNOSIS APPARATUS

CROSS-REFERENCE TO RELATED APPLICATION

This application is based upon and claims the benefit of priority from Japanese Patent Application No. 2011-021601, filed Feb. 3, 2011; the entire contents of which are incorporated herein by reference.

FIELD

The embodiment of the present invention is related to an ultrasound diagnosis technology.

BACKGROUND

An ultrasound diagnosis apparatus transmits ultrasound waves to the inside of a subject using an ultrasound probe, and acquires organism information of the subject by receiving the reflected waves.

Ultrasound diagnosis apparatuses are used in examinations of various body sites. In these examinations of body sites, different examination conditions are applied in each case. Examination conditions refer to various conditions that are selectively applied based on the examination type (examination sites and examination details). Examples of examination conditions include image quality conditions and applications, etc. Examination conditions are set in advance, and are also referred to as "pre-sets".

Image quality conditions (image quality pre-sets) are parameters for adjusting the image quality of ultrasound images being displayed. Examples include gains in received signals, dynamic range, input-output relations for brightness modulation, raster counts for raster smoothing processes, frame counts for frame smoothing processes, sound pressure of transmitted ultrasound, transmission frequency, repetition frequency, frame rate, and scan sequences, etc.

Applications (application pre-sets) are application software that are selectively used according to the examination type. Examples include applications for cardiac examinations, applications for fetal examinations, and examination protocols, etc. Applications for cardiac examinations are used to analyze the size (area, volume, length, etc.) and wall motion, etc. of a heart during a cardiac examination. Applications for fetal examinations are used to analyze the size and cardiac function of a fetus during an examination of a pregnant female. Examination protocols define examination procedures and setting conditions according to the workflow of an examination, and may be set for each hospital or each physician.

Image quality conditions for obtaining good images differ depending on the ultrasound probe being used and the examination type. Applications are also used selectively according to the examination type, etc. In conventional ultrasonic diagnosis apparatuses, by preparing tables associating examination types with pre-sets, pre-sets are used selectively according to the examination type designated by the examiner at the start of an examination.

In ultrasound examinations, multiple body sites may be examined. In such a case, the examiner re-selects a pre-set each time the examined region is changed. This reduces the efficiency of the examination.

Thus, it is intended to provide with an ultrasound diagnosis apparatus that enables multiple body sites to be examined efficiently.

DETAILED DESCRIPTION

The ultrasound diagnosis apparatus according to the embodiment will be described with reference to the drawings.

Figure 1:
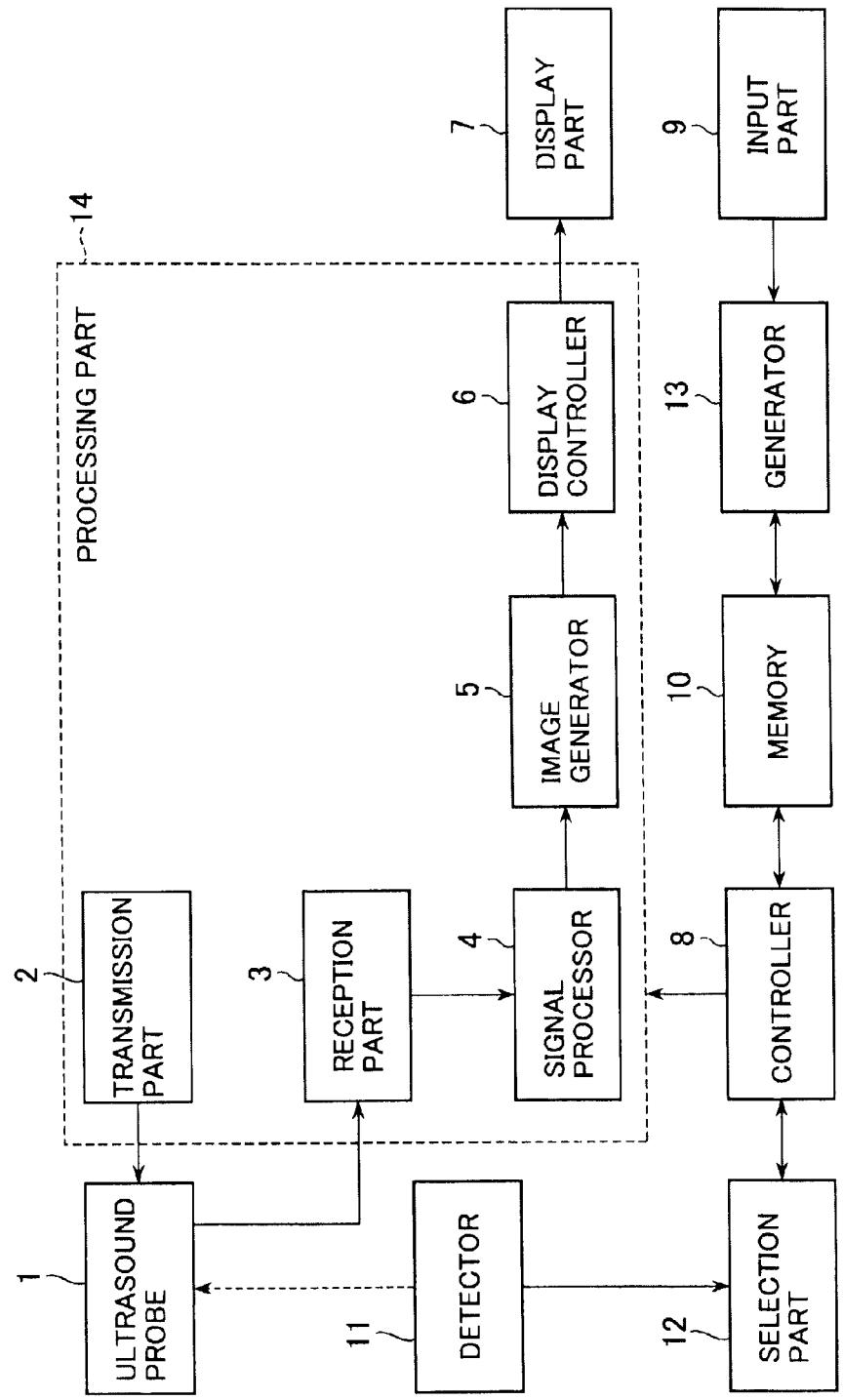
FIG. 1 is an outline block diagram showing the ultrasound diagnosis apparatus according to the embodiment.

An example configuration of the ultrasound diagnosis apparatus according to the embodiment will be described. As shown in FIG. 1, the ultrasound diagnosis apparatus according to the embodiment includes an ultrasound probe 1, a transmission part 2, a reception part 3, a signal processor 4, an image generator 5, a display controller 6, a display part 7, a controller 8, an input part 9, a memory 10, a detector 11, a selection part 12, and a generator 13. The transmission part 2, the reception part 3, the signal processor 4, the image generator 5, and the display controller 6 are collectively referred to as the processor 14.

For the ultrasound probe 1, a one-dimensional array probe in which multiple ultrasound transducers are arranged in one row in the scanning direction, or a two-dimensional array probe in which multiple ultrasound transducers are arranged two-dimensionally is used. Moreover, a mechanical one-dimensional probe may be used that causes multiple ultrasound transducers arranged in one row in the scanning direction to oscillate in an oscillation direction perpendicular to the scanning direction. The ultrasound probe 1 transmits ultrasound waves to the subject, and receives reflected waves from the subject as echo signals.

The position of the ultrasound probe 1 is detected by the detector 11. As the details will be described later, the ultrasound probe 1 is provided with a configuration for realizing position detection by the detector 11.

The transmission part 2 feeds electrical signals to the ultrasound probe 1 and causes it to transmit ultrasound waves that have been beam-formed to a prescribed focal point (i.e., that have been transmission beam formed).

The reception part 3 receives echo signals received by the ultrasound probe 1. The reception part 3 receives echo signals received by the ultrasound probe 1, and by performing a delay process on the echo signals, converts analog echo signals into phased (i.e., reception beam formed) digital data.

The reception part 3 includes, for example, a preamp (preamplifier) circuit, an A/D converter, a reception delay circuit, and an adder that are not illustrated. The preamp circuit amplifies echo signals output from each ultrasound transducer of the ultrasound probe 1 for each reception channel. The A/D converter converts the amplified echo signals into digital signals. The reception delay circuit assigns the echo signals converted into digital signals a delay time required for determining the reception directivity. The adder adds the echo signals that have been assigned a delay time. As a result of this addition, reflected components from the direction corresponding to the reception directivity are emphasized. Received signals output from the reception part 3 are output to the signal processor 4.

The signal processor 4 includes a B-mode processor. The B-mode processor receives the received signals from the reception part 3, and performs imaging of the amplitude information of the received signals. Specifically, the B-mode processor performs a band-pass filtering process on the received signals, and then detects the envelope curve of the output signals and performs a compression process on the detected data through logarithmic conversion.

The signal processor 4 may include a CFM (Color Flow Mapping) processor. The CFM processor performs imaging of blood flow information. Blood flow information includes information such as velocity, distribution, or power, etc. and blood flow information is obtained as binarized information.

The signal processor 4 may include a Doppler processor. The Doppler processor retrieves Doppler-shifted frequency components by phase-detecting the received signals, and generates a Doppler frequency distribution showing the blood flow velocity by performing an FFT process.

The signal processor 4 outputs the received signals that have undergone signal processing (ultrasound raster data) to the image generator 5.

The image generator 5 generates ultrasound image data based on the signal-processed received signals (ultrasound raster data) output from the signal processor 4. The image generator 5 includes, for example, a DSC (Digital Scan Converter). The image generator 5 converts the signal-processed received signals shown in signal rows of the scanning line into image data represented in an orthogonal coordinate system (scan conversion process). For example, by performing a scan conversion process on the received signals that have undergone signal processing by the B-mode processor, the image generator 5 generates B-mode image data showing the morphology of the tissue of the subject. The image generator 5 outputs the ultrasound image data to the display controller 6.

The display controller 6 receives the ultrasound image data from the image generator 5, and causes the display part 7 to display an ultrasound image based on the ultrasound image data. Moreover, the display controller 6 receives a control from the controller 8, and causes the display part 7 to display various screens and information.

The display part 7 is configured by a monitor such as a CRT or a liquid crystal display. The display part 7 displays ultrasound images. Moreover, the display part 7 displays various screens and information.

The controller 8 controls the operations of each part of the ultrasound diagnosis apparatus. In particular, the controller 8 receives selection results from the selection part 11, and controls each part included in the processor 14. Moreover, the controller 8 writes and reads out information and data into and from the memory 10.

The input part 9 receives operations by the user, and inputs signals and information corresponding to the operation details into the controller 8. In particular, the input part 9 inputs body-type information (described in detail later) of the subject. The controller 8 receives these signals and information and controls each part. Moreover, the input part 9 may include a function for receiving inputs of signals and information via a network or media.

The memory 10 stores various information and data, as well as computer programs. For example, the memory 10 stores association information generated by the generator 13. This association information associates positions in real space with examination conditions. The association information has the format of table information, for example. Furthermore, the association information is generated before the implementation of each examination. The process of generating the association information and controls based thereon will be described later.

Real space refers to actual space, and in particular, this includes the space where the subject is arranged. Generally, the subject is placed on a bed in a body posture corresponding to the examination details. In this case, the real space is set to include the top surface of the bed and the surrounding space. Moreover, the real space may be set as the range in which the position detection by the detector 11 (described later) is possible. Furthermore, considering the fact that the subject of detection by the detector 11 is the ultrasound probe 1 (or the scan cross-section), the real space need only include the range of positions of the detection subject during the ultrasound examination.

As described above, examination conditions refer to various conditions that are selectively applied according to the examination type. Examination conditions include at least either or both image quality conditions and/or application type.

The detector 11 detects the position of the ultrasound probe 1 in real space. This position may include the orientation (angle) of the ultrasound probe 1 (i.e., the irradiation direction of the ultrasound waves). In this case, the detector 11 may be the to detect a cross-sectional position of the subject being scanned by the ultrasound probe 1. The cross-sectional position can be obtained based on the position and orientation of the ultrasound probe 1. Moreover, if information on the depth of the cross-section is required, this may be calculated by considering the determining factors of the invasion depth of the ultrasound waves in the body (i.e., the intensity and wavelength, etc. of the ultrasound waves). Furthermore, processes for obtaining the cross-sectional position from the position of the ultrasound probe 1 may be performed by the detector 11, or may be performed by the selection part 12 or the generator 13.

The detector 11 is configured by including a position sensor such as, for example, a magnetic sensor or an optical sensor. If a magnetic sensor is applied, for example, a magnetic field source that generates a magnetic field is provided in the ultrasound probe 1, and a detector that detects the magnetic field generated by this magnetic field source is arranged at a prescribed position in real space. If an optical sensor is applied, for example, a light source that emits light is provided in the ultrasound probe 1, and a detector that detects light from this light source is arranged at a prescribed position in real space. In either configuration, the detector obtains the position of the magnetic field source or light source in real space (i.e., the position of the ultrasound probe 1 in real space) based on the detection results of the magnetic field or light as well as its own position in real space.

It should be noted that the detector 11 is not limited to these, and any configuration may be used as long as the position of the ultrasound probe 1 in real space can be detected. The detector 11 feeds the detection results of the position of the ultrasound probe 1 (or the scan cross-section) into the selection part 12.

The selection part 12 receives the detection results of the position of the ultrasound probe 1 from the detector 11, and selects the examination conditions corresponding to these detection results based on the association information. More specifically, the selection part 12 of the present embodiment receives the detection results of the position of the ultrasound probe 1 from the detector 11, and selects the examination conditions corresponding to these detection results based on the body-type information input from the input part 9 and the association information. The selection part 12 inputs the selected examination conditions into the controller 8. The controller 8 controls the processor 14 based on the examination conditions input from the selection part 12. As a result, processing based on the image quality conditions and application type shown in these examination conditions is executed. Furthermore, details of the examination-conditions selection part 12 will be described below.

The generator 13 generates association information based on information input from the input part 9. Details of the generator 13 will be described later.

Figure 2:
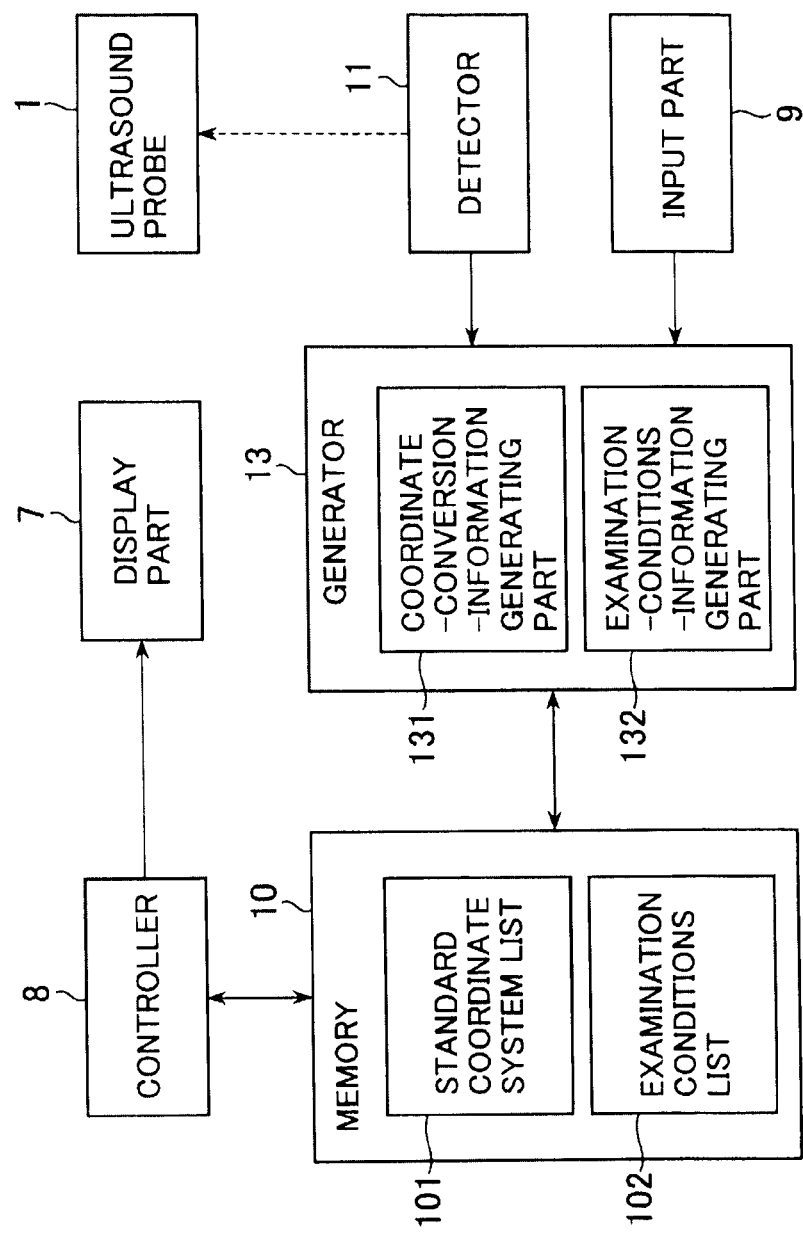
FIG. 2 is an outline block diagram showing the ultrasound diagnosis apparatus according to the embodiment.

Configurations related to the generation of association information will be described with reference to FIG. 2.

At the time of starting the process of generating association information, no association information is stored in the memory 10. At the time of starting this process, as shown in FIG. 2, a standard coordinate system list 101 and an examination conditions list 102 are already stored.

The standard coordinate system list 101 is information associating the body posture of the subject placed on the bed with standard coordinate systems. Examples of body posture include a supine position (state of lying on one's back), a prone position (state of lying on one's stomach), a right lateral recumbent position (state of lying on one's right side), and a left lateral recumbent position (state of lying on one's left side). The standard coordinate system list 101 associates each of these body postures with a standard coordinate system.

A standard coordinate system is a coordinate system that has been preliminarily set in relation to real space. The scale (length of a unit distance in each coordinate axis) of the standard coordinate system is preliminarily set based on, for example, standard body-height information and standard body-width information. Standard body-height information refers to a standard body height (e.g., mean body height). Standard body-width information refers to a standard body width. For the standard body-width information, mean body weight, mean waist circumference, mean chest circumference, or mean shoulder width, etc. is used. Furthermore, if information that does not directly represent body width, such as mean body weight, is used, the body width corresponding to the mean body weight, etc. is obtained based on, for example, clinical data showing the relationship between body weight, etc. and body width, and this is used as the standard body-width information.

Furthermore, if the subject is arranged on their side, the body width information represents the thickness of the body. Consequently, in this embodiment, body width refers to the length of the subject in the horizontal direction perpendicular to the body-height direction of the subject when they are lying down on a bed. In other words, in this embodiment, body width may be the to refer to the length of the subject in the width direction of the bed.

The examination conditions list 102 is synopsis information of examination conditions (image quality conditions and/or application type) that can be applied by the ultrasound diagnosis apparatus according to the present embodiment. The examination conditions list 102 may be synopsis information (a list) of multiple examination conditions, or may categorize multiple examination conditions. Examples of this categorization include the following: (1) categorization between image quality conditions and application types; (2) categorization based on the type of image quality conditions (gains in received signals, dynamic range, input-output relations for brightness modulation, raster counts for raster smoothing processes, frame counts for frame smoothing processes, sound pressure for ultrasound signals, transmission frequency, repetition frequency, frame rate, and scan sequences, etc.; (3) categorization based on application type (applications for cardiac examinations, applications for fetal examinations, examination protocols, etc.); and (4) categorization based on body sites (chest, abdominal region, heart, liver, stomach, intestine, etc.).

These categories may be mutually exclusive, or may be categories based on considerations of inclusive relations. Examples of exclusive categories include categorization based on "chest" and "abdominal region". Moreover, examples of categorization based on considerations of inclusive relations include the combined use of classifications for each organ ("heart", "liver", etc.) and classifications for each site ("chest", "abdominal region", etc.).

As described above, the generator 13 generates association information. The generator 13 receives information input from the input part 9 as well as information representing the position of the ultrasound probe 1 detected by the detector 11. Furthermore, the generator 13 reads out information stored in the memory 10. The generator 13 is provided with a coordinate-conversion-information generator 131 (first generator) and an examination-conditions-information generator 132 (second generator).

Figure 3:
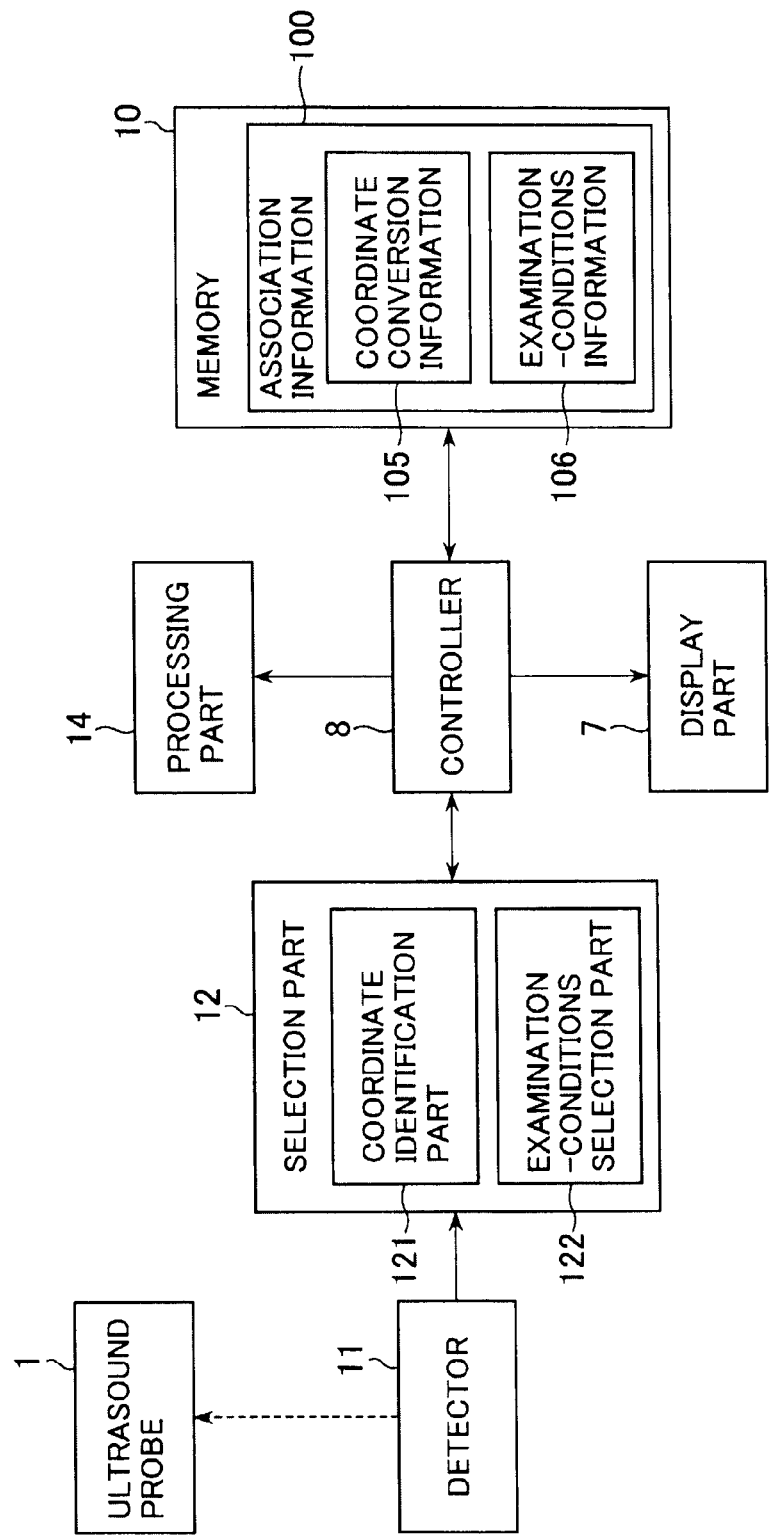
FIG. 3 is an outline block diagram showing the ultrasound diagnosis apparatus according to the embodiment.

The coordinate-conversion-information generator 131 generates the coordinate conversion information 105 (first association information) shown in FIG. 3 based on information input from the input part 9. The input part 9 of the present embodiment inputs body-type information of the subject into the coordinate-conversion-information generator 131. Body-type information refers to information representing the body type of the subject. The coordinate-conversion-information generator 131 calculates the scale ratio between the standard coordinate system and the subject coordinate system based on the input body-type information. Furthermore, the coordinate-conversion-information generator 131 generates coordinate conversion information 105 based on the calculated scale ratio.

The subject coordinate system is a coordinate system that is set uniquely for each subject. Each subject has a unique body type. Consequently, there is a unique positional relationship between the examination site of the subject and the position of the ultrasound probe 1 in real space. The subject coordinate system is generated by performing coordinate conversion that takes into consideration this unique positional relationship on the standard coordinate system.

An example method of generating the coordinate conversion information 105 (i.e., a method of generating the subject coordinate system) will be described. In the present example, body-height information and body width information (body weight, etc.) of the subject is input as the body-type information. This body-type information is input by operating a keyboard or touch panel, etc. in the input part 9, for example. Moreover, the body-type information may be acquired and input automatically from electronic chart information of the subject. If applying this configuration, the input part 9 includes a configuration (e.g., the controller 8) that retrieves electronic chart information. Furthermore, the mode of input for body-type information is not limited to these.

Moreover, the input part 9 inputs the body-posture information of the subject into the coordinate-conversion-information generator 131. Body-posture information refers to information showing the body posture of the subject during the examination. Body-posture information that can be input includes the supine position, prone position, right lateral recumbent position, and left lateral recumbent position, etc. described in the standard coordinate system list 101. The coordinate-conversion-information generator 131 reads out the standard coordinate system list 101 stored in the memory 10, and selects a standard coordinate system corresponding to the input body-posture information.

Furthermore, the coordinate-conversion-information generator 131 sets the subject coordinate system based on the selected standard coordinate system and the input body-height information and body width information. An example of this process is described below. Furthermore, the standard coordinate system is defined by two or three coordinate axes, including the coordinate axis in the body-axis direction (height direction) of the subject lying on the bed and the coordinate axis in the body-width direction.

The coordinate-conversion-information generator 131 calculates the ratio of the body-height information of the subject relative to the standard body-height information (the scale ratio of the body-height direction). Then, the coordinate-conversion-information generator 131 multiplies the value of the calculated scale ratio by the scale of the coordinate axis in the body-height direction of the standard coordinate system. As a result, the scale of the coordinate axis in the body-height direction of the subject coordinate system is determined. The scale of the coordinate axis in the body-width direction of the subject coordinate system is determined in a similar manner. In this way, the subject coordinate system is set.

Furthermore, if a three-dimensional coordinate system is used as the subject coordinate system, an arbitrary coordinate axis set for the height direction that is perpendicular to both the coordinate axis in the body-height direction and the coordinate axis in the body-width direction is used. For this coordinate axis in the height direction, one that is set in advance for the standard coordinate systems (three-dimensional coordinate systems) is used, for example. Moreover, a configuration may be used in which an input of body-type information including the size of the subject in the height direction (i.e., body thickness in the supine or prone position, or body width in the right or left lateral recumbent positions) is received, and the scale of the coordinate axis in the height direction in the subject coordinate system is determined based on this body-type information and the value of pre-set standard body thickness or body width.

The standard coordinate system, the scale ratios of the coordinate axes, and the subject coordinate system are in a relationship in which if any two are determined, the remaining one is also automatically determined. Furthermore, because the standard coordinate system is provided in advance, the scale ratios and the subject coordinate system are in a relationship in which if one is determined, the other is also determined. Consequently, based on the assumption that the standard coordinate system has been provided, the scale ratios and the subject coordinate system can be considered as one. In other words, determination of the scale ratios and setting of the subject coordinate system can be considered the same.

Moreover, in the coordinate-conversion-information generator 131, standard position information in real space is input from the input part 9. This standard position information indicates positions in real space corresponding to standard coordinates in the standard coordinate system. These standard coordinates are coordinates that act as standards for positions in the standard coordinate system. A typical example of standard coordinates is the origin point of the standard coordinate system. Moreover, the movement range of the ultrasound probe 1 is limited, and because the range that can be detected by the detector 11 is also limited, a standard coordinate system of limited size can be set. In this case, a prescribed position in the edges of the standard coordinate system can be defined as the standard coordinates. Moreover, if the standard coordinate system is set based on standard body-height information, etc., the position in the standard coordinate system corresponding to a prescribed body site (e.g., the umbilicus or the nose, etc.) in the standard body type may be defined as the standard coordinates.

Examples of methods of inputting standard position information will be described. In the first example, the abovementioned detector of the detector 11 is placed at a prescribed position of the subject placed on a bed, and an operation for establishing this placement position as the standard position is performed using the input part 9. In the second example, the detector of the detector 11 is arranged at an arbitrary position in real space, and the displacement between the position of the detector and the position corresponding to the standard coordinates (the displacement in the standard coordinate system) is obtained. Then, upon receiving an operation on the input part 9, the position of the detector and the displacement are input together as the standard position information. Furthermore, if an operation for establishment using the input part 9 is not necessary, a signal from the detector becomes the standard position information. In this case, the detector functions as the input part.

When standard coordinate information is input, it is possible to associate a desired position in real space with the respective standard coordinates (origin points, etc.) of the standard coordinate system and the subject coordinate system. As a result, positions in real space are associated with coordinates in the coordinate systems considered in the present embodiment. In this way, the input of standard coordinate information acts to associate real space with coordinate systems. Because the determination of scale ratios corresponds to coordinate conversion between the standard coordinate system and the subject coordinate system, the coordinate conversion information 105 is intended to associate positions in real space with coordinates in the subject coordinate system, and is also intended to associate positions in real space with coordinates in the standard coordinate system. Processes of generating the coordinate conversion information 105 such as those described above are performed at the time of an examination (immediately before an ultrasound examination, etc.) of a subject, for example.

The examination-conditions-information generator 132 generates the examination-conditions information 106 (second association information) associating regions in the standard coordinate system with examination conditions. This process is performed at an arbitrary timing before an examination, for example.

The process of generating the examination-conditions information 106 is performed by using or not using the ultrasound probe 1. If the process is performed without using the ultrasound probe 1, a prescribed display screen or a user interface of the input part 9, etc. is used. A specific example of this user interface will be described later.

A similar user interface is also used when using the ultrasound probe 1. The user arranges the ultrasound probe 1 at a desired position within real space. The position of this ultrasound probe 1 (or the scan cross-section position) is detected by the detector 11. The detection results are input into the generator 13. Furthermore, it is assumed that the abovementioned input of standard position information has already been performed, and association between real space and the standard coordinate system has already been performed. The examination-conditions-information generator 132 identifies the region within the standard coordinate system (examination region) that corresponds to the position of the ultrasound probe detected by the detector 11.

In the first example of this process, multiple positions are designated while moving the position of the ultrasound probe 1. The detector 11 detects these multiple positions. The examination-conditions-information generator 132 determines the coordinates within the standard coordinate system that correspond to each detected position. Furthermore, the examination-conditions-information generator 132 determines a closed curve that passes through the multiple determined coordinates. This closed curve is, for example, a spline curve or a Bezier curve. The regions enclosed by this closed curve become the examination regions designated based on the multiple detection positions.

In the second example, circles are drawn with the coordinates corresponding to each individual detection position of the ultrasound probe 1 in the center, and the regions enclosed by these circles are defined as the examination regions. The method of setting the radius of these circles is arbitrary. For example, the user may designate a desired radius, or a default value for the radius may be used. This default value is set in advance according to, for example, the size of the subject (organ, site, etc.) being examined.

Furthermore, the examination-conditions-information generator 132 associates each set examination region with one of the examination conditions included in the examination conditions list 102. This process may be performed manually by the user, or may be performed automatically by the examination-conditions-information generator 132.

As an example of a case of manual operation, the list of examination conditions is displayed on the display part 7 as a pull-down menu, for example. Then, by using the input part 9, the user designates the desired examination conditions from the displayed list. At this time, instead of displaying all of the examination conditions included in the examination conditions list 102, it is possible to selectively display examination conditions suitable for the body site corresponding to the examination region. In this case, regions corresponding to each body site in a standard body type are set in advance in the standard coordinate system. Moreover, the examination conditions included in the examination conditions list 102 are categorized by body site (described above). The examination-conditions-information generator 132 identifies the region in the standard coordinate system within which the examination region is contained, and displays a list of examination conditions categorized under the body site corresponding to the identified region. The user operates the input part 9 and selects the desired examination conditions from the list. By performing these processes for each examination region, the examination-conditions information 106 is generated.

As an example of a case in which the examination conditions are selected automatically, examination conditions used in past (e.g., the previous) examinations of the subject are acquired from electronic chart information, and these conditions are also applied in the current examination. This example is likely to be useful when examining a single site multiple times, such as for follow-up observations and pre- and post-operative observations. Moreover, it is likely to be useful also for cases in which examinations of specific body sites are mainly being performed, or for cases in which diagnosis of a specific disease is being performed. Another example will now be described. In this example, as with the case described for manual operation, when the examination conditions included in the examination conditions list 102 are categorized by body site, examination conditions corresponding to the examination region are automatically selected. At this time, if there is only one set of examination conditions corresponding to the examination region, this set of examination conditions is associated with the examination region. If there are multiple examination regions, for example, the disease name is acquired from the electronic chart information, etc., and examination conditions that should be applied to patients with this disease are associated. Furthermore, information (table information, etc.) in which disease names are associated with examination conditions is stored in advance in the memory 10. By performing the above processes for each examination region, the examination-conditions information 106 is generated.

If multiple examination regions have been set, several of those examination regions may overlap. For example, after observing the entire chest with one set of examination conditions, if observing the heart with another set of examination conditions, the examination region for the heart is included in the examination region for the entire chest. Moreover, when examining the heart from different angles for example, the corresponding multiple examination regions will be partially overlapped together. In such cases, it would be useful if it were possible to set which examination region to observe with priority from among the examination regions with overlaps. For example, it would be useful to be able to set an examination sequence when setting two or more examination regions sharing a superimposed region, and to sequentially switch between examination conditions according to the examination sequence. The following is a description of a configuration for realizing such a process.

The user operates the input part 9 and designates a priority sequence for two or more examination regions having a superimposed region. The designation results are input from the input part 9 into the examination-conditions-information generator 132. The examination-conditions-information generator 132 associates the designation results of the priority sequence input from the input part 9 with the two or more examination regions and generates the examinations-conditions information 106. The method of designating the priority sequence will be described later.

During an examination, if the position of the ultrasound probe 1 is detected by the detector 11, the selection part 12 (the examination-conditions selection part 121, described later) determines whether the coordinates corresponding to the detection position are contained in the superimposed region. Furthermore, the coordinates of each examination region are already known, so this determination process is easy. If it is determined that the coordinates corresponding to the detection position are contained in the superimposed region, the selection part 12 identifies the examination region of the highest priority sequence from among the two or more examination regions, and selects the examination conditions corresponding to the identified examination region. As a result, it is possible to examine the superimposed region using the examination region with the highest priority sequence. Furthermore, the switching of the examination region may be performed by operating the input part 9, or may be performed automatically according to the detection position of the ultrasound probe 1. As a result, it is possible to sequentially switch between examination conditions according to the set priority sequence, and to examine two or more examination regions having a superimposed region.

The association information created as described above is used during examinations. In the following, a configuration that operates during examinations is described with reference to FIG. 3. As shown in FIG. 3, at the time of commencement of an examination, the association information 100 is stored in the memory 10. The association information 100 includes the coordinate conversion information 105 and the examination-conditions information 106. Furthermore, the coordinate conversion information 105 associates position in real space with coordinates in the subject coordinate system (and the standard coordinate system). Moreover, the examination-conditions information 106 associates examination regions in the standard coordinate system with examination conditions. Consequently, by referring to the association information 100, it becomes possible to associate positions in real space with examination conditions through coordinate conversion between the standard coordinate system and the subject coordinate system.

Based on the association information 100, the selection part 12 selects examination conditions corresponding to positions of the ultrasound probe 1 (or scan cross-sections) detected by the detector 11. This process is executed by the coordinate identification part 121 and the examination-conditions selection part 122.

Based on the coordinate conversion information 105, the standard coordinate system that has been preliminarily set with regard to real space is converted into the subject coordinate system of the subject. The coordinate identification part 121 receives the detection results of the position of the ultrasound probe 1 from the detector 11. These detection results are coordinates in the subject coordinate system. The coordinate identification part 121 identifies the coordinates in the standard coordinate system that correspond to the coordinates in the subject coordinate system based on the coordinate conversion information 105. In other words, by converting detection regions of the ultrasound probe 1 using the coordinate conversion information 105, the coordinate identification part 121 obtains coordinates corresponding to the detection regions in the standard coordinate system. Information on the acquired coordinates is input into the examination-conditions selection part 122.

The examination-conditions selection part 122 receives the information on the coordinates acquired by the coordinate identification part 121. Then, based on the examination-conditions information 106, the examination-conditions selection part 122 selects examination conditions corresponding to the examination regions in the standard coordinate system in which the coordinates are contained. This process is divided into a process of identifying the examination regions and a process of selecting the examination conditions. The former identifies examination regions in which coordinates identified by the coordinate identification part 121 are contained in the standard coordinate system. The latter identifies examination conditions corresponding to the examination regions identified in the former process by referring to the examination-conditions information 106.

It is possible to monitor the position of the ultrasound probe 1 during an examination and sequentially switch between examination conditions in accordance with temporal changes in the position (i.e., with movements of the ultrasound probe 1). For this purpose, the detector 11 periodically detects the position of the ultrasound probe 1. In order to be able to detect the position of the ultrasound probe 1 substantially in real time, the time interval for position detection is set by considering, for example, the movement velocity of the ultrasound probe 1. This time interval may be set based on factors that affect the movement velocity of the ultrasound probe 1. Such factors include individual differences between users, or level of skill in the examination, etc. Moreover, this time interval may also be set arbitrarily through a manual process. Moreover, this time interval may also be a prescribed default value. The detection results that are thus obtained periodically are input into the selection part 12 each time detection is performed.

Each time detection results of the position are input from the detector 11, the selection part 12 performs the abovementioned process of selecting examination conditions. The selection part 14 sends the selection results for the examination conditions to the controller 8. Furthermore, the selection results may be sent to the controller 8 only if the examination conditions selected in this selection process differ from those selected previously. The controller 8 controls the processor 14 based on the selected examination conditions to causes it to execute processing according to the examination conditions.

By using such a configuration, if examination conditions identical to those selected previously are selected, the processor 14 continues the processing according to these examination conditions. Alternatively, if new examination conditions different from those selected previously are selected, the processing based on the previous examination conditions is ended, and processing based on the new examination conditions is started.

As described above, the processor 14 is configured by including the transmission part 2, the reception part 3, the signal processor 4, the image generator 5, and the display controller 6. Under control by the controller 8, each of these parts 2-6 performs operations according to examination conditions selected by the selection part 12.

An example of operations of the ultrasound diagnosis apparatus according to the present embodiment will be described. In the following, the processing executed by the ultrasound diagnosis apparatus is divided into pre-processing and processing performed during examinations. Moreover, an example of the user interface will also be described.

Figure 4:
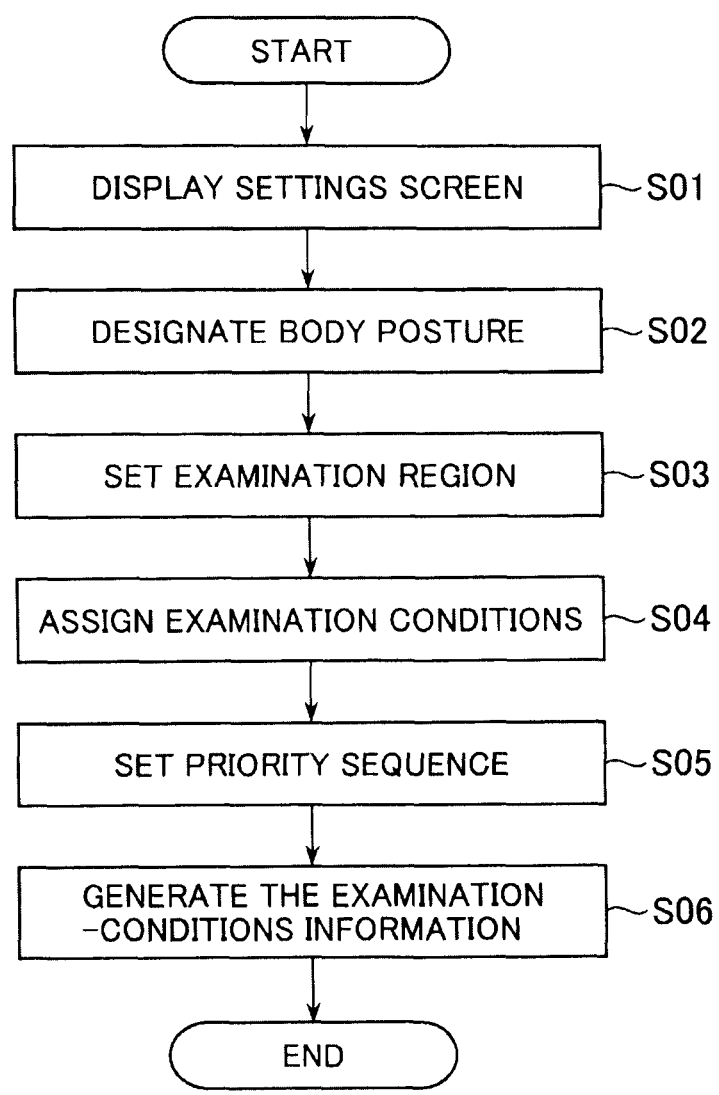
FIG. 4 is a flowchart showing operations of the ultrasound diagnosis apparatus according to the embodiment.

An example of pre-processing is shown in FIG. 4. The pre-processing generates the common examination-conditions information 106 that does not differ between subjects. Pre-processing is performed at an arbitrary timing before an examination, for example. When performing pre-processing, the subject does not have to be placed on the bed. At the start time of pre-processing, the standard coordinate system list 101 and the examination conditions list 102 are stored in the memory 10 as shown in FIG. 2, and the association information 100 is not yet stored.

First, the user operates the input part 9 to issue an instruction for a settings screen to be displayed. Upon receiving this instruction, the controller 8 reads out data for the settings screen (not illustrated) that has been stored in advance in the memory 10, and causes the display part 7 to display the settings screen (S01). This settings screen is a user interface used for displaying information required for pre-processing and for inputting information.

Figure 5:
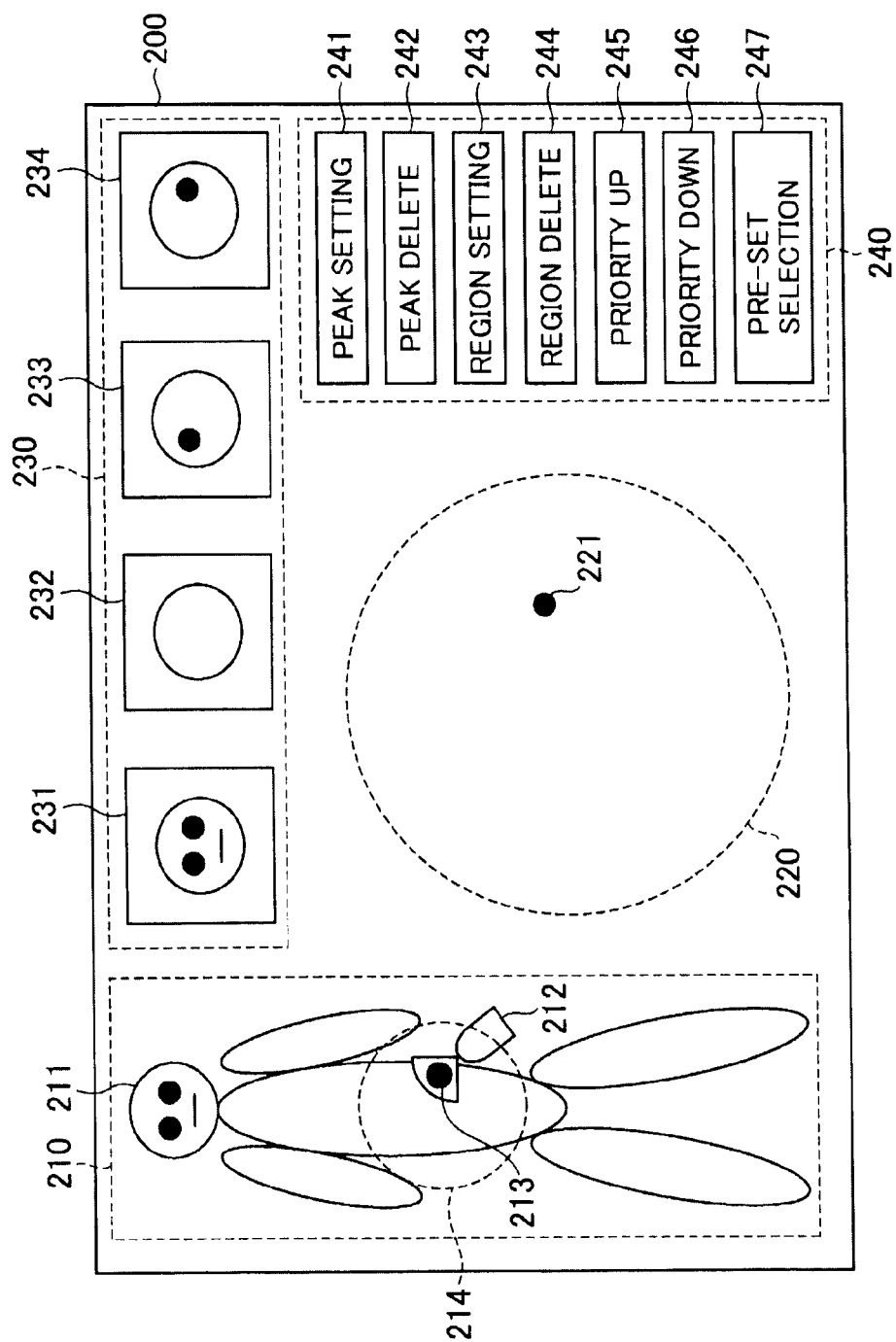
FIG. 5 is an outline diagram showing a settings screen displayed by the ultrasound diagnosis apparatus according to the embodiment.

An example of the settings screen is shown in FIG. 5. Here, the description of the operational example is interrupted to describe the configuration of the settings screen 200. The settings screen 200 is provided with an overall display part 210, a settings operation part 220, a body-posture designation part 230, and a button part 240.

The overall display part 210 displays the body posture of the subject, the position of the ultrasound probe 1, and scan cross-section positions. The overall display part 210 also displays a subject image 211, a probe image 212, a cross-section position image 213, and an examination site image 214, etc. Furthermore, at the time that the settings screen 200 is displayed in step S01, these images 211-214 do not have to be displayed yet, or such standard information may be displayed.

The subject image 211 is a schematic diagram resembling a human body. The memory 10 stores subject image data in advance for each option for body posture. The displayed subject image 211 is selected according to the designation results for body posture from the body-posture designation part 230.

The probe image 212 shows the position of the ultrasound probe 1. The display position of the probe image 212 is determined based on the detection results from the detector 11. Moreover, in cases such as performing pre-processing without actually using the ultrasound probe 1, a configuration may be used in which the display position of the probe image 212 can be changed using the input part 9 (e.g., a pointing device such as a mouse).

The cross-section position image 213 shows cross-section positions of the subject being scanned by the ultrasound probe 1. As described above, the detector 11 of this operational example detects the position of the ultrasound probe 1 and detects cross-section positions based on those positions. Moreover, in cases such as performing pre-processing without actually using the ultrasound probe 1, as with the probe image 212, it is possible to use a configuration in which the display position of the cross-section position image 213 can be changed using the input part 9.

The examination site image 214 shows a region in the overall display part 210 that is magnified and displayed in the settings operation part 220. The examination site image 214 is displayed at the position in the overall display part 210 corresponding to the position of the ultrasound probe 1. The display position of the examination site image 214 is, for example, set for each relatively large category of body site (abdominal region, chest, etc.). An example of a process for selecting and displaying the examination site image 214 may be: determining coordinates of the standard coordinate system from the detection results of the position of the ultrasound probe 1; identifying the body site corresponding to these coordinates; and selecting and displaying the examination site image corresponding to this body site. Furthermore, the display position and size of the examination site image 214 may be set in advance, or may be set arbitrarily by the user.

The settings operation part 220 is displays various information for setting the association information 100. The details displayed in the settings operation part 220 corresponds to the region contained in the examination site image 214. The settings operation part 220 shown in FIG. 5 displays the cross-section position image 221. The display position of the cross-section position image 221 in the settings operation part 220 corresponds to the display position of the cross-section position image 213 in the examination site image 214. Furthermore, at the time of displaying the settings screen 200 in step S01, the cross-section position image 221 is not yet displayed.

The body-posture designation part 230 is used for designating the body posture of the subject. As options for body posture, the body-posture designation part 230 is provided with a supine position button 231, a prone position button 232, a right lateral recumbent position button 233, and a left lateral recumbent position button 234. Each button 231-234 is a software key (icon). The user operates the input part 9 and designates the desired button 231-234. Examples of this designation method include click operations using a pointing device (not illustrated).

The button part 240 is provided with various buttons used for setting the association information 100. The button part 240 of this operational example is provided with a peak setting button 241, a peak delete button 242, a region setting button 243, a region delete button 244, a priority raising button 245, a priority lowering button 246, and a pre-set selection button 247.

The peak setting button 241 is used for setting a peak for setting an examination region. The peak delete button 242 is used for deleting a peak that has been set. The region setting button 243 is used for setting an examination region. The region delete button 244 is used for deleting an examination region that has been set. The priority raising button 245 and the priority lowering button 246 are used for setting the priority sequence (priority) of two or more examination regions. The priority raising button 245 is used for raising the priority sequence of a specific examination region, and the priority lowering button 246 is used for lowering the priority sequence. The pre-set selection button 247 is used for assigning a pre-set (examination conditions) to an examination region. Each button 241-247 is a software key (icon). By operating a pointing device and clicking a desired button, for example, the user issues an instruction for the operation corresponding to that button. With the above, the description of the configuration of the settings screen 200 is ended, and we return to the description of the operational example. Furthermore, for the user interface, the settings screen 200 is used.

As described above, at the time of displaying the settings screen 200, it is not necessary to display the subject image 211, the probe image 212, the cross-section position image 213, the examination site image 214, and the cross-section position image 221. By clicking any of the buttons 231-234 of the body-posture designation part 230, the user designates the body posture of the subject (S02). In the present operational example, the supine position button 231 is clicked.

When the supine position button 231 is clicked, the controller 8 causes the overall display part 210 to display the subject image 211 corresponding to the supine position (refer to FIG. 5). Moreover, the generator 13 acquires the standard coordinate system corresponding to the selected body posture (supine position) from the standard coordinate system list 101. The positions in the overall display part 210 are associated with coordinates in the standard coordinate system.

Next, the examination region is set. As described above, the setting of the examination region is performed while operating the ultrasound probe 1 or the input part 9 (pointing device, etc.). The present operational example describes a case of using the input part 9. Furthermore, if the ultrasound probe 1 is used, instead of designating the position using the input part 9, the examination region is set based on the detection results of the position of the ultrasound probe 1 from the detector 11 (S03).

The user operates the input part 9 to designate a desired examination site in the subject image 212 displayed in the overall display part 210. The controller 8 causes the examination site image 214 corresponding to the designated examination site to be displayed. Moreover, the controller 8 associates the region enclosed by the examination site image 214 with the region in the settings operation part 220.

Furthermore, the user operates the input part 9 to set the examination region in the settings operation part 220. An example of this operation will be described. Through a click operation of a pointing device, the user designates a desired position within the settings operation part 220. The controller 8 causes the cross-section position image 221 to be displayed at the designated position, and also causes the cross-section position image 213 to be displayed at the corresponding position in the overall display part 210 (refer to FIG. 5). Furthermore, the desired position in the subject image 211 may be designated.

The user determines whether the positions of the cross-section position images 213, 221 are suitable. This determination is made by referring to the position of the cross-section position image 213 in the subject image 211, for example. At this time, in the subject image 211, images showing the standard positions of various organs may be displayed. If the designated positions are suitable, the user operates the input part 9 and clicks the peak setting button 241. In response to this operation, the examination-conditions-information generator 132 records the coordinates in the standard coordinate system corresponding to the scan cross-section position.

Figure 6:
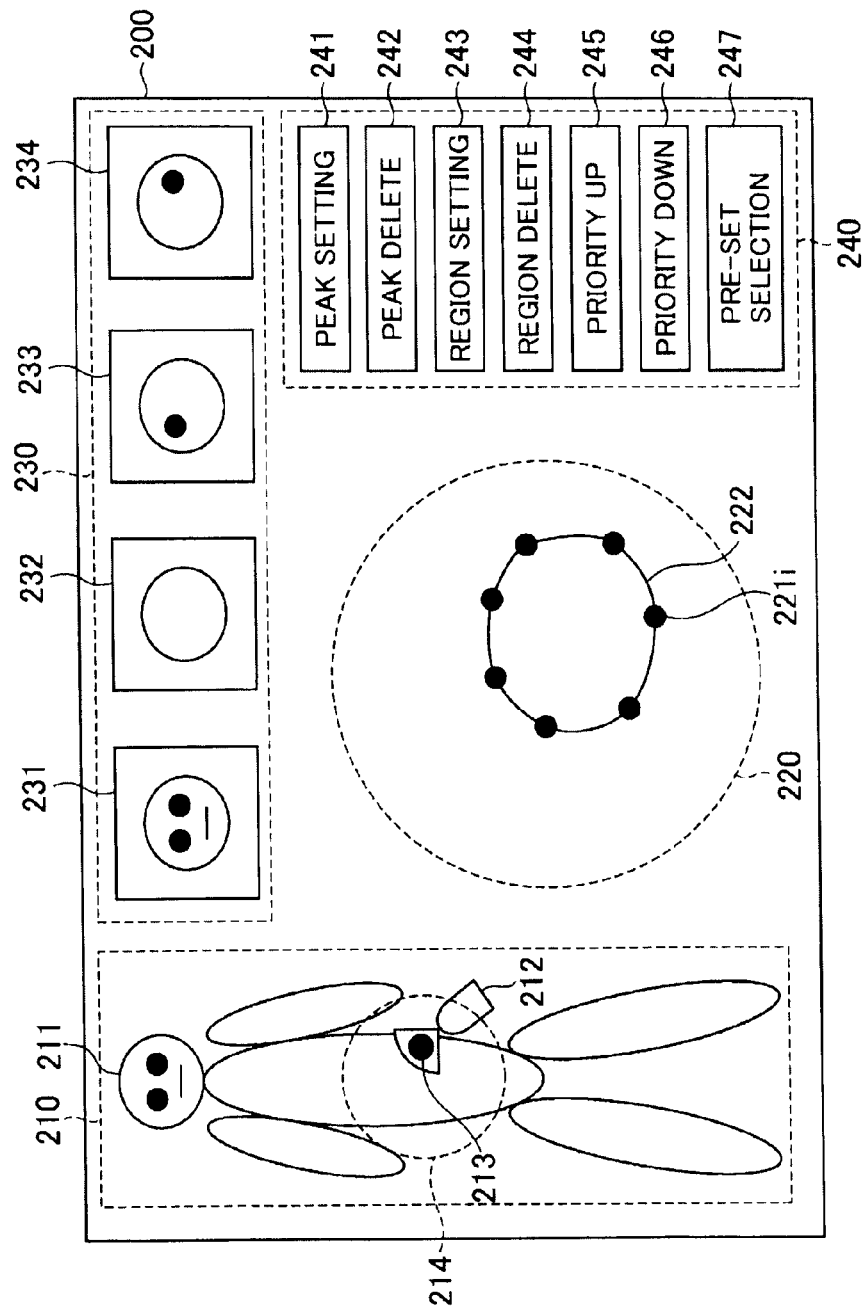
FIG. 6 is an outline diagram for describing operations of the ultrasound diagnosis apparatus according to the embodiment.

By repeating the above processes, multiple scan cross-section positions are recorded. Then, the user clicks the region setting button 243. Upon receiving this, the examination-conditions-information generator 132 obtains a closed curve (spline curve, etc.) that connects these scan cross-section positions. Based on the obtained multiple scan cross-sections and the closed curve, the controller 8 causes the cross-section position image 221$i$ (i=1 to M, wherein M is the number of scan cross-section positions) and closed curve image 222 shown in FIG. 6 to be displayed in the settings operation part 220. The region enclosed by the closed curve image 222 becomes the examination region. Furthermore, the display of the cross-section position image 221$i$ may be omitted to display only the closed curve image 222.

Another method of setting examination regions will be described. The user sets a single scan cross-section position and clicks the region setting button 243. The examination-conditions-information generator 132 sets a circular region having this scan cross-section position as its center and also has a prescribed radius as an examination region. Moreover, it is also possible to configure the examination region as designated through drag operations of the pointing device. Furthermore, it is also possible to use a configuration in which icons corresponding to examination regions of various shapes are provided in the settings screen 200 and the examination region is set through the designation of a desired icon and the designation of the position and size of the examination region.

Figure 7:
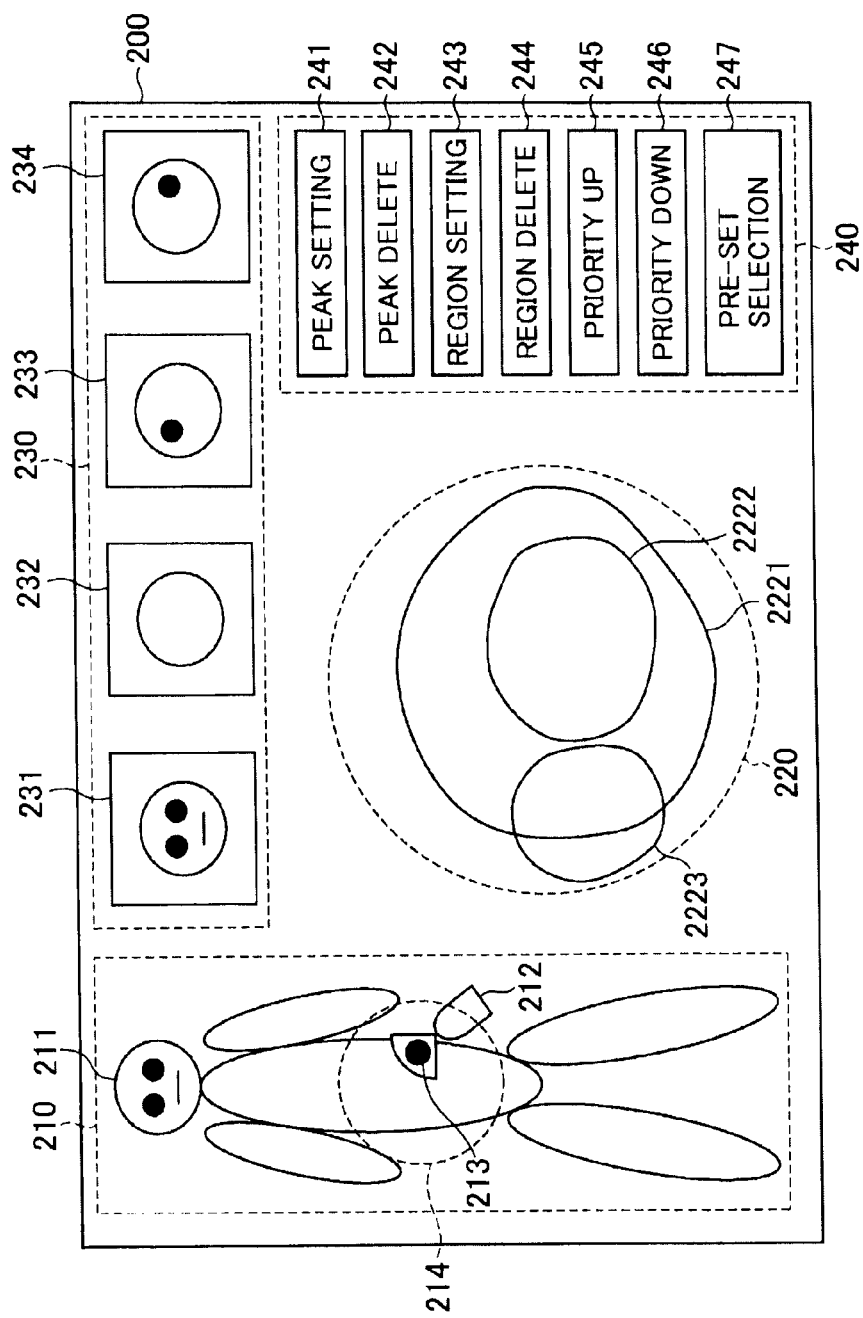
FIG. 7 is an outline diagram for describing operations of the ultrasound diagnosis apparatus according to the embodiment.

By repeating the above processing, the user sets a desired number of examination regions. An example of the display mode at this time is shown in FIG. 7. In the settings operation part 220 of FIG. 7, three examination regions 2221, 2222, 2223 are displayed. The examination region 2221 is, for example, for broadly examining the abdominal region. Moreover, the examination regions 2222, 2223 are, for example, for examining sites of particular note in the abdominal region. Furthermore, in FIG. 7, illustrations of the cross-section position images are omitted.

When the setting of the examination regions is completed, examination conditions are assigned to each examination region (S04). For this purpose, first, the user designates one of the examination regions 2221-2223. This designation operation involves, for example, clicking a desired examination region.

Next, the user clicks the pre-set selection button 247. Upon receiving this, the controller 8 selects examination conditions corresponding to the designated examination region (e.g., the abdominal region) from the examination conditions list 102, and causes the display part 7 to display a list thereof. The user clicks the desired examination conditions from the displayed list. The examination-conditions-information generator 132 associates the selected examination conditions with the designated examination region. Furthermore, if it is possible to narrow down the examination conditions corresponding to the designated examination region to one set (e.g., if there is only one set of corresponding examination conditions), the examination-conditions-information generator 132 may automatically assign those examination conditions without displaying the above list.

The above processing is performed for each examination region. As a result, examination conditions are assigned to each of the three examination regions 2221, 2222, 2223.

In the present operational example, because the set examination regions 2221, 2222, 2223 have a superimposed region, a priority sequence is set as necessary (S05). As an example, the user clicks any examination region to set the priority sequence of this examination region by using the priority raising button 245 and the priority lowering button 246. Furthermore, if there is no superimposed region, it is not necessary to perform this step S08.

By associating each examination region set in step S03 with the examination conditions designated in step S04 and the priority sequence set in step S05, the examination-conditions-information generator 132 generates the examination-conditions information 106 (S06). The examination-conditions-information generator 132 causes the memory 10 to store this examination-conditions information 106 as the association information 100. Furthermore, if selectively using multiple items of the examination-conditions information 106 during an examination, each item of the examination-conditions information 106 is assigned an ID, and these are linked and stored in the memory 10. With the above, the description of pre-processing in the present operational example is finished.

Figure 8:
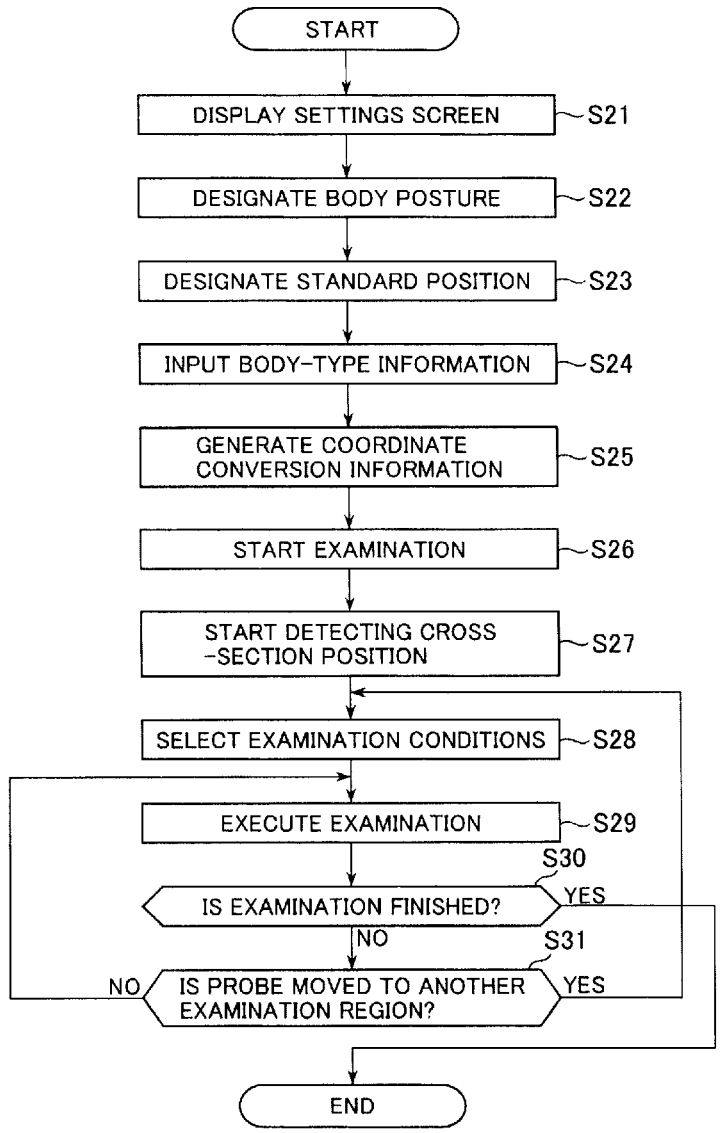
FIG. 8 is a flowchart showing operations of the ultrasound diagnosis apparatus according to the embodiment.

An example of processing during an examination is shown in FIG. 8. On the bed, the subject is arranged in a body posture for examination. Moreover, at a prescribed position (i.e., a standard position in real space) of the subject, the detector parts of the detector 11 are arranged. The controller 8 reads out the examination-conditions information 106 from the memory 10 and sends it to the selection part 12. In the following, the examination regions 2221, 2222, 2223 shown in FIG. 7 are examined. For the priority sequence, the examination region 2221 has the highest priority, followed by the examination region 2222 and then finally the examination region 2223. For processing during an examination, before an actual examination, a setting process unique to the subject is performed. This setting process is for generating the coordinate conversion information 105 of the subject.

First, the user operates the input part 9 to issue an instruction for the settings screen 200 to be displayed. Upon receiving this instruction, the controller 8 causes the settings screen 200 to be displayed (S21).

From among the buttons 231-234 of the body-posture designation part 230, the user clicks the button corresponding to the body posture of the subject during the examination (S22). The controller 8 causes the overall display part 210 to display the subject image 211 corresponding to the designated body posture (refer to FIG. 5, etc.). Moreover, the controller 8 selects the standard coordinate system corresponding to the designated body posture from the standard coordinate system list 101.

Next, a standard position is designated. The standard position is a position in real space corresponding to standard coordinates in the standard coordinate system. In the present operational example, the detector parts of the detector 11 are arranged at a prescribed position of the subject, and furthermore, by operating the input part 9, this prescribed position is established as the standard position (S23). Based on the standard position information from the input part 9 (or the detector), the coordinate-conversion-information generator 131 associates the standard coordinates in the standard coordinate system selected in step S22 with the standard position (the above prescribed position) in real space. As an example of this process, if the detector is arranged on the umbilicus of the subject, this position on the umbilicus is associated with the origin point of the standard coordinate system.

Next, body-type information of the subject is input (S24). The body-type information of the present operational example includes body-height information and body-weight information.

As described above, the standard coordinate system is set based on the standard body-height information and the standard body-width information (standard body-weight information). The coordinate-conversion-information generator 131 calculates the ratio between the standard body-height information and the body-height information and calculates the ratio between the standard body-weight information and the body-weight information. Furthermore, the coordinate-conversion-information generator 131 generates the coordinate conversion information 105 based on these scale ratios (S25). The generated coordinate conversion information 105 is stored in the memory 10 as the association information 100.

Figure 9:
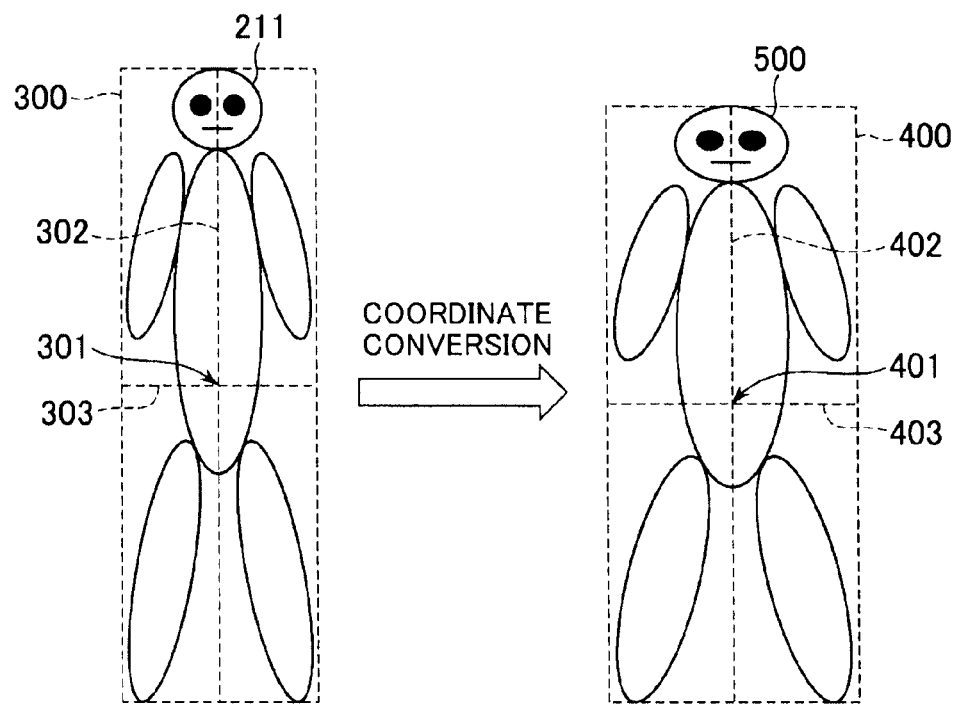
FIG. 9 is an outline diagram for describing operations of the ultrasound diagnosis apparatus according to the embodiment.

An outline of coordinate conversion based on scale ratios is shown in FIG. 9. The standard coordinate system 300 uses the origin point 301 as the standard position, and has a limited region corresponding to a standard body type. In other words, the coordinate axis 302 in the body-axis direction has a length corresponding to the standard body-height information, and the coordinate axis 303 in the body-width direction has a length corresponding to the standard body-width information (standard body-weight information). For the coordinates in the standard coordinate system 300, for example, the origin point 301 is (0, 0), and the top left, top right, bottom left and bottom right corners of the limited region are (−1, −1), (1, −1), (−1, 1) and (1, 1), respectively.

By multiplying the coordinate axes 302, 303 of the standard coordinate system 300 by the above scale ratios, the subject coordinate system 400 is obtained. In other words, by multiplying the coordinate axis 302 in the body-axis direction of the standard coordinate system 300 by the scale ratio for body height, the coordinate axis 402 of the subject coordinate system 400 is obtained. The coordinate axis 403 in the body-width direction is obtained in a similar manner. The origin point 401 is the intersection of the coordinate axes 402, 403.

As with the coordinates of the standard coordinate system 300, the coordinates of the subject coordinate system 400 are defined so that the origin point 401 is (0, 0), and the top left, top right, bottom left and bottom right corners of the limited region are (−1, −1), (1, −1), (−1, 1) and (1, 1), respectively. The coordinates (0, 0) of the origin point 401 are associated with the standard position in real space (i.e., the position of the detector) through the coordinates (0, 0) of the origin point 301 of the standard coordinate system 300. Furthermore, this association is based on the standard position information. In this way, the coordinate conversion information 105 of the present operational example incorporates the standard position information. The subject image 500 applies the scale ratios to the standard subject image 211. Furthermore, in the present operational example, it is sufficient as long as the subject coordinate system 400 is obtained, and it is not necessary to create the subject image 500.

The display mode of the overall display part 210 may be any mode that allows the position of the ultrasound probe 1 (scan cross-section position) relative to the subject to be recognized. Consequently, the subject image 211 displayed in the settings screen 200 may be an image showing a standard body type, or it may be the subject image 500 obtained by applying the scale ratios to this image. Furthermore, because the standard coordinate system 300 and the subject coordinate system 400 have been associated using the coordinate conversion information 105, regardless of which image is displayed, there is no particular effect on the display of the overall display part 210.

In the present operational example, based on the coordinate conversion information 105, the coordinate system in real space is switched from the standard coordinate system 300 to the subject coordinate system 400. As a result, the subject coordinate system 400 corresponding to the body type of the subject placed on the bed is set in real space. Then, positions in real space obtained as coordinates in the subject coordinate system 400 are converted to coordinates in the standard coordinate system 300 using the coordinate conversion information 105, and examination conditions are selected. After making the above preparations, the process shifts to the actual examination.

The user places the ultrasound probe I against the body surface of the subject (S26). At this time, it is common to place the ultrasound probe 1 in contact within the examination region 2221 that has the highest priority sequence.

The detector 11 periodically detects the position of the ultrasound probe 1 (i.e., the scan cross-section) (S27). As a result, the detector 11 monitors movements of the ultrasound probe 1.

The selection part 12 determines whether the detection region from step S27 is contained within any of the detection regions 2221-2223 (in this case, based on the inclusive relations, the detection region 2221). If it is determined not to be contained in the detection region 2221, the selection part 12 stands by until the detection region is contained in the detection region 2221. The user moves the ultrasound probe 1 so that the detection region is determined to be contained in the examination region 2221. Furthermore, in this case, prescribed examination conditions may be set. Moreover, if the subject for examination has been preliminarily identified as the examination regions 2221-2223, the examination conditions corresponding to the examination region 2221 that has the highest priority sequence may be selected, for example.

On the other hand, if it is determined that the detection results of the scan cross-section position are contained in the examination region 2221, the selection part 12 determines whether the detection region is contained in a superimposed region. If it is determined not to be contained in a superimposed region (i.e., if the detection region is contained in the examination region 2221 but outside the examination regions 2222, 2223), the selection part 12 refers to the examination-conditions information 106 and selects examination conditions corresponding to the examination region 2221.

Moreover, if it is determined that the detection region is contained in a superimposed region, the selection part 12 identifies the examination region 2221 that has the highest priority sequence based on the abovementioned priority sequence. Then, the selection part 12 refers to the examination-conditions information 106, and selects the examination conditions corresponding to the examination region 2221 (S28).

The examination conditions selected by the selection part 12 are input into the controller 8. The controller 8 controls the processor 14 based on the examination conditions. As a result, it is possible to perform an examination of the examination region 2221 with the examination conditions corresponding to the examination region 2221. At this stage, the examination is continued (S30: NO; S31: NO).

When the examination of the examination region 2221 is ended, the ultrasound probe 1 is moved so that the scan cross-section position is contained in the next examination region. The movement of the scan cross-section position is detected by the detector 11 (S31: YES). Furthermore, in the present operational example, because the examination region 2221 that includes the examination regions 2222, 2223 is examined first, it may be determined that the examination of the examination region 2221 has ended in response to an instruction from the user. Furthermore, changes in the examination region in subsequent stages may be performed automatically in response to movements of the scan cross-section position.

The detector 11 monitors movements of the scan cross-section position. In response to the scan cross-section position entering the examination region 2222, the selection part 12 selects corresponding examination conditions (S28). The selection results are sent to the controller 8. The controller 8 causes the processor 14 to execute processing based on these new examination conditions. As a result, the operational mode of the processor 14 switches from processing based on the examination conditions for the examination region 2221 to processing based on the examination conditions for the examination region 2222 (S29). Until the scan cross-section position moves to another examination region, this processing is continued (S30: NO; S31: NO).

The detector 11 continues to monitor movements of the scan cross-section position. In response to the scan cross-section position entering the examination region 2223, the selection part 12 selects corresponding examination conditions (S28). The controller 8 causes the processor 14 to execute processing based on these new examination conditions, so as to switch the operational mode of the processor 14 from processing based on the examination conditions for the examination region 2222 to processing based on the examination conditions for the examination region 2223 (S29). Until the examination of this final examination region 2223 is ended, this processing is continued (S30: NO; S31: NO). When the examination of the examination region 2223 ends, the processing of the present operational example also ends (S30: YES).

The effects of the ultrasound diagnosis apparatus according to the present embodiment will be described.

During an examination, the ultrasound diagnosis apparatus according to the present embodiment stores the association information 100 that associates positions in real space with examination conditions. The detector 11 detects the position of the ultrasound probe 1 (i.e., the scan cross-section position) in real space. The selection part 12 selects examination conditions corresponding to the detection region from the detector 11 based on the association information 100. The processor 14 performs processing based on the examination conditions selected by the selection part 12.

According to this type of embodiment, it is possible to automatically switch the examination conditions in accordance with the position of the ultrasound probe 1, and it is therefore not necessary to re-select examination conditions each time the examination site is changed. Consequently, it becomes possible to efficiently perform examinations of multiple body sites. Furthermore, as described above, the examination conditions include image quality conditions and applications. By automatically selecting image quality conditions according to examination site, it is possible to obtain images of good quality while making examinations more efficient. Moreover, by automatically selecting applications according to examination site, it is possible to efficiently perform examinations according to the examination type or workflow corresponding to the examination site.

Moreover, by periodically detecting the scan cross-section position, the detector 11 of the present embodiment monitors movements thereof. The selection part 12 selects examination conditions each time the detector 11 performs position detection. In response to the selection of new examination conditions different from the previous selection by the selection part 12, the processor 14 starts processing based on the new examination conditions. According to this type of embodiment, in response to the ultrasound probe 1 being moved to another examination region, the examination conditions automatically switch to conditions corresponding to the new examination region. Consequently, it is no longer necessary for the user to make changes to the examination conditions that accompany changes in the examination region, and it becomes possible to make examinations more efficient.

Moreover, the association information 100 of the present embodiment is generated based on standard position information in real space corresponding to standard coordinates in the standard coordinate system, as well as on the body-type information of the subject. As a result, it becomes possible to automatically identify examination conditions according to the body type of the subject arranged at an arbitrary position in real space. Consequently, it is possible to select examination conditions with a high degree of certainty regardless of the position of the subject in real space or the body type of the subject.

A variation of the above embodiment will now be described. The following variation is related to the switching of examination conditions that accompanies movements of the ultrasound probe 1.

The present variation is applied in cases in which there are adjacent examination regions. (i.e., in cases which the first examination region and the second examination region share a boundary, or in cases in which there is a first and second examination region that share a superimposed region.)

By periodically detecting the position of the ultrasound probe 1 (the scan cross-section position), the detector 11 monitors movements of the ultrasound probe 1. The selection part 12 identifies the examination region that contains the coordinates corresponding to the position detected periodically by the detector 11. Upon detecting that the identified examination region has switched from the first examination region to the second examination region, the examination-conditions selection part 122 determines whether the distance between the coordinates corresponding to the position detected by the detector 11 and the boundary of the first and second examination regions (or the boundary of the superimposed region) is equal to or greater than a prescribed distance. This prescribed distance is set in advance according to the detection interval, etc. of the detector 11. Furthermore, in response to the distance becoming equal to or greater than the prescribed distance, the examination-conditions selection part 122 selects examination conditions corresponding to the second examination region. Upon receiving this selection result, the controller 8 switches the operational mode of the processor 14 to a mode for the first examination region to a mode for the second examination region.

Figure 10:
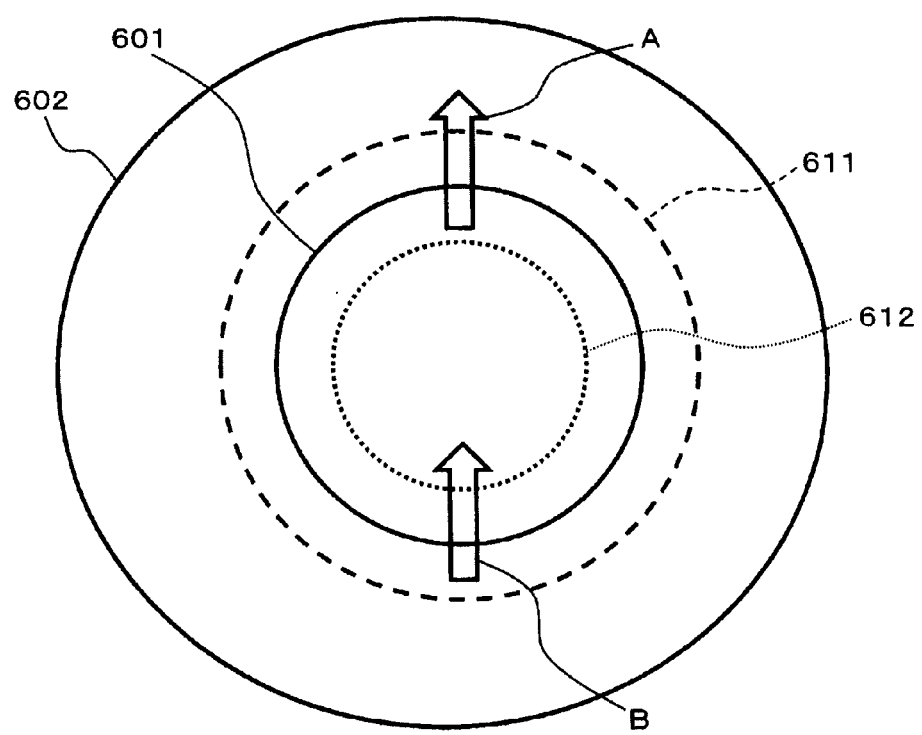
FIG. 10 is an outline diagram for describing a variation of the embodiment.

An example of this processing will be described with reference to FIG. 10. The two examination regions 601, 602 shown in FIG. 10 share a superimposed region. Furthermore, the processing details are the same for cases in which the examination regions are adjacent to each other.

Because the examination region 601 is part of the examination region 602, the boundary between these regions is the boundary (i.e., the outer border) of the examination region 601. A first switching boundary 611 is set at a position that is at a prescribed distance inside the examination region 602 from the boundary. Similarly, a second switching boundary 612 is set at a position that is at a prescribed distance inside the examination region 601 from the boundary. Furthermore, the two "prescribed distances" may be equal, or they may be different. The arrows A, B show the direction of movement of the ultrasound probe 1 (the scan cross-section position).

If the ultrasound probe 1 is moved in the direction of the arrow A, the examination region 601 becomes the above first examination region, and the examination region 602 becomes the above second examination region. When the ultrasound probe 1 moving in the direction of the arrow A exceeds the boundary of the examination region 601, the examination region identified by the selection part 12 switches from the examination region 601 to the examination region 602.

Subsequently, each time position detection is performed by the detector 11, the examination-conditions selection part 122 calculates the distance between the coordinates corresponding to the detection region and the boundary with the examination region 601, and determines whether this distance is equal to or greater than the prescribed distance. If this distance becomes equal to or greater than the prescribed distance, the examination-conditions selection part 122 selects examination conditions corresponding to the examination region 602 based on the association information 100. Upon receiving this selection result, the controller 8 switches the operational mode of the processor 14 from a mode for the examination region 601 to a mode for the examination region 602.

Similarly, if the ultrasound probe 1 is moved in the direction of the arrow B, once the ultrasound probe 1 is moved a prescribed distance into the examination region 601 from the boundary of the examination region 601, the operational mode of the processor 14 is switched from a mode for the examination region 602 to a mode for the examination region 601.

According to this type of variation, it is possible to smoothly switch examination conditions at the boundaries of examination regions. Moreover, it is possible to perform the examination of the examination region preceding the switch in examination conditions up to the boundary with certainty.

Next, another variation will be described. In the above embodiment, when examination conditions corresponding to the detected position are selected, processing is performed based on the selected examination conditions, but the selection examination conditions may be displayed on the display part and provided for confirmation by the operator.

Moreover, in the above embodiment, a specific ultrasound probe was the subject, but examination conditions (e.g. the image quality conditions and application type) may be changed according to the probe type (convex, linear, sector, etc.). Further, while the above embodiments describes selecting examination conditions based on detected positions, examination conditions may be selected based on a combination of the probe used for imaging and the detected positions. Specifically, the procedure may include: reducing the number of examination conditions based on the detected positions; and selecting one of the reduced examination conditions using the probe used for the imaging etc.

Further, the procedure may include: reducing the number of examination conditions based on the detected positions or the probe used for the imaging; displaying some reduced examination conditions; and selecting one of the examination conditions displayed on the display part 7 based on the operation via the input part.

While certain embodiments have been described, these embodiments have been presented by way of example only, and are not intended to limit the scope of the inventions. Indeed, the novel systems described herein may be embodied in a variety of their forms; furthermore, various omissions, substitutions and changes in the form of the systems described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus that includes an ultrasound probe that transmits and receives ultrasound waves to and from a subject, and generates and displays images based on reception results from the ultrasound probe, comprising:
    a memory that stores association information indicating association of a diagnosis region of the subject with at least one examination condition comprising at least one of image quality conditions, and an application used for diagnosis of the diagnosis region;
    a probe position sensor configured to obtain position information of the probe on a surface of the subject;
    a detector configured to detect one diagnosis region based on the obtained position information of the ultrasound probe;
    a user interface configured to input body-type information of the subject; and
    processing circuitry configured to select, from a plurality of possible examination conditions, at least one examination condition associated with the at least one diagnosis region detected by the detector based on the association information stored in said memory, and configured to perform the transmission and reception waves and the image generation based on the selected at least one examination condition, and wherein
    the association information includes:
        first association information that associates positions in the real space with coordinates in a subject coordinate system set for the subject; and
        second association information that associates each of a plurality of diagnosis regions in the standard coordinate system with the examination conditions, and wherein
    the processing circuitry identifies coordinates in the standard coordinate system corresponding to the position detected by the detector based on the first association information and the input body-type information, and selects examination conditions corresponding to the region in the standard coordinate system containing the identified coordinates based on the second association information.

2. The ultrasound diagnosis apparatus according to claim 1, wherein
    the coordinate identification part identifies coordinates in the subject coordinate system corresponding to the detected position based on the first association information, and identifies coordinates in the standard coordinate system corresponding to the identified coordinates in the subject coordinate system based on the body-type information.

3. The ultrasound diagnosis apparatus according to claim 1, wherein
    the detector is configured to periodically detect the position,
    the processing circuitry is configured to select the examination conditions each time the position is detected by the detector, and when new examination conditions different from before is selected by the processing circuitry, the processor starts processing based on the selected new examination conditions.

4. The ultrasound diagnosis apparatus according to claim 2, wherein the detector periodically is configured to detect the position, and
   if a first region and a second region from among the plurality of regions share a boundary or include a superimposed region, the processing circuitry performs:
   determining whether the distance between the coordinates corresponding to the position detected by the detector and either the boundary or the boundary of the superimposed region is equal to or greater than a prescribed distance, after the region containing the coordinates corresponding to the periodically detected position switches from the first region to the second region, and
   selecting examination conditions corresponding to the second region when the determined distance becomes equal to or greater than the prescribed distance.

5. The ultrasound diagnosis apparatus according to claim 1, further comprising:
   a user interface configured to input body-type information of the subject and standard position information in the real space corresponding to standard coordinates in a pre-set standard coordinate system; and
   a generator configured to generate the association information based on the input standard position information and body-type information.

6. The ultrasound diagnosis apparatus according to claim 1, further comprising:
   a first generator configured to set the subject coordinate system based on the input body-type information and the standard coordinate system, and to generate the first association information based on the set subject coordinate system.

7. The ultrasound diagnosis apparatus according to claim 6, wherein
   the first generator is configured to set the subject coordinate system by changing the scale of the standard coordinate system based on the input body-type information.

8. The ultrasound diagnosis apparatus according to claim 7, wherein
   the scale of the standard coordinate system is preliminarily set based on standard body-height information and standard body-width information,
   the user interface is configured to input body-height information and body width information of the subject as the body-type information, and
   the first generator is configured to calculate the ratio between the standard body-height information and the body-height information as well as the ratio between the standard body-width information and the body width information, and to change the scale based on the values of these ratios.

9. The ultrasound diagnosis apparatus according to any one of claims 6 through 8, wherein
   the memory preliminarily stores a plurality of the standard coordinate systems corresponding to a plurality of body postures,
   the user interface is configured to input body posture information of the subject,
   the first generator is configured to select a standard coordinate system corresponding to the input body posture information from among the plurality of standard coordinate systems, to set the subject coordinate system based on the selected standard coordinate system, and to generate the first association information for the subject coordinate system.

10. The ultrasound diagnosis apparatus according to claim 6, wherein
    the memory preliminarily stores a plurality of the examination conditions, and
    the user interface is configured to input standard position information in the real space corresponding to standard coordinates in the standard coordinate system, the ultrasound diagnosis apparatus further comprising:
    a second generator configured to identify a region in the standard coordinate system based on the position of the ultrasound probe detected by the detector and the input standard position information, and to generate the second association information by associating this region with any of the plurality of examination conditions.

11. The ultrasound diagnosis apparatus according to claim 10, wherein
    the user interface is configured to input a priority sequence for two or more regions including a superimposed region from among the plurality of regions,
    the second generator is configured to associate this input priority sequence with the two or more regions to generate the second association information, and
    if the coordinates corresponding to the position detected by the detector are contained in the superimposed region, the processing circuitry is configured to select the examination conditions corresponding to the region ranked highest in the priority sequence from among the two or more regions.

12. The ultrasound diagnosis apparatus according to claim 1, wherein
    the detector comprises a magnetic sensor or an optical sensor.

13. The ultrasound diagnosis apparatus according to claim 1, wherein the position detected by the detector comprises information on the position and orientation of the ultrasound probe.

14. An ultrasound diagnosis method that transmits and receives ultrasound waves by means of an ultrasonic probe to and from a subject and generates images, including:
    storing association information indicating association of a diagnosis region of the subject with at least one examination condition comprising at least one of image quality conditions and an application used for diagnosis of the diagnosis region;
    obtaining position information indicating the position of the ultrasound probe on a surface of the subject;
    detecting at least one diagnosis region based on the obtained position information indicating the position of the ultrasound probe;
    selecting, from a plurality of possible examination conditions, at least one examination condition associated with the at least one diagnoses region detected by the detector based on the association information stored in said memory; and
    performing the transmission and reception of the ultrasound waves and the image generation based on the selected at least one examination condition.

15. An ultrasound diagnosis method according to claim 14, wherein the selecting and performing steps comprise:
    selecting as the at least one examination condition at least one of image quality condition based on the association information stored in said memory performing the transmission and reception of the ultrasound waves based on the selected at least one of image quality condition.

16. An ultrasound diagnosis method according to claim 14, wherein the selecting and performing steps comprise:
selecting as the at least one examination condition an application used for diagnosis of the diagnosis region based on the association information stored in said memory
performing the image generation based on the selected application used for diagnosis of the diagnosis region.

* * * * *